United States Patent [19]

Cummings et al.

[11] Patent Number: 4,598,579

[45] Date of Patent: Jul. 8, 1986

[54] PORTABLE INSTRUMENT TO TEST PRESSURE/FLOW OF VENTRICULAR SHUNT VALVES

[75] Inventors: Joel Cummings, Ocala; Michael D. Hooven, Miami, both of Fla.

[73] Assignee: Cordis Corporation, Miami, Fla.

[21] Appl. No.: 663,871

[22] Filed: Oct. 23, 1984

[51] Int. Cl.$^4$ .......................................... G01M 19/00
[52] U.S. Cl. ......................................... 73/37; 73/4 R; 73/168; 604/9
[58] Field of Search ................ 73/168, 4 R, 37; 604/9

[56] References Cited

U.S. PATENT DOCUMENTS

| | | | |
|---|---|---|---|
| 2,569,299 | 9/1951 | Fegel | 73/4 R |
| 3,098,382 | 7/1963 | Hoffman et al. | 73/168 |
| 3,886,948 | 6/1975 | Hakim | 604/9 |
| 3,894,541 | 7/1975 | El-Shafel | 604/10 |
| 4,156,442 | 5/1979 | Hildebrandt et al. | 128/748 |
| 4,342,218 | 8/1982 | Fox | 73/4 R |
| 4,387,591 | 6/1983 | Colzine et al. | 73/168 |
| 4,450,710 | 5/1984 | Nettekoven | 73/168 X |
| 4,515,012 | 5/1985 | Jenkins et al. | 73/168 |
| 4,546,642 | 10/1985 | Swanson | 73/168 X |

FOREIGN PATENT DOCUMENTS

| | | | |
|---|---|---|---|
| 1197184 | 7/1970 | United Kingdom | 73/168 |
| 194378 | 5/1967 | U.S.S.R. | 73/168 |
| 212930 | 5/1968 | U.S.S.R. | 73/168 |
| 501169 | 4/1976 | U.S.S.R. | 73/168 |
| 728864 | 4/1980 | U.S.S.R. | 73/168 |

OTHER PUBLICATIONS

"Non-Contaminating Pneumatic Testing"; Bulletin 4074; American Instrument Co. Inc. of Silverspring, MD; Jan. 1961; 1 page.
Crodis publication entitled ¢Hakin-Valve System for Ventriculo-Atristomy"; Oct. 1965; 18 pages.
Validyne CD23 Digital Transducer Indicator Brochure & Validyne Pressure Transducer D15/DP215 Brochure; Both on same 1 page; by Nov. 1983.
"Hydrocephalus Correction"; *Handbook of Biomedical Plastics;* published by Mar. 19895; pp. 8-11 through 8-14 and 8-18; Henry Lee & Kris Neville.
Sage Instruments Model 341A Syringe Pump Brochure; 1 page; published by Mar. 1985.

*Primary Examiner*—Stewart J. Levy
*Assistant Examiner*—Tom Noland
*Attorney, Agent, or Firm*—Lockwood, Alex, Fitzgibbon & Cummings

[57] ABSTRACT

A portable instrument system is provided for the testing of pressure and flow characteristics of implantable ventricular shunt valves using a gaseous testing fluid that may be drawn from the testing environment. The system includes a rate pump having a control mechanism that provides a variety of selective constant flow rates so that the valve characteristics can be determined under various operating conditions. Fluid communication is provided between the pump, the valve and a pressure sensing device such that the pressure sensing device receives the same pressure and flow rate that the valve does. Typically, the pressure sensing device is a gauge transducer that utilizes atmospheric pressure as a reference point and senses the changes in the gas pressure in the valve, relaying the pressure readings to a digital display or chart recorder.

18 Claims, 4 Drawing Figures

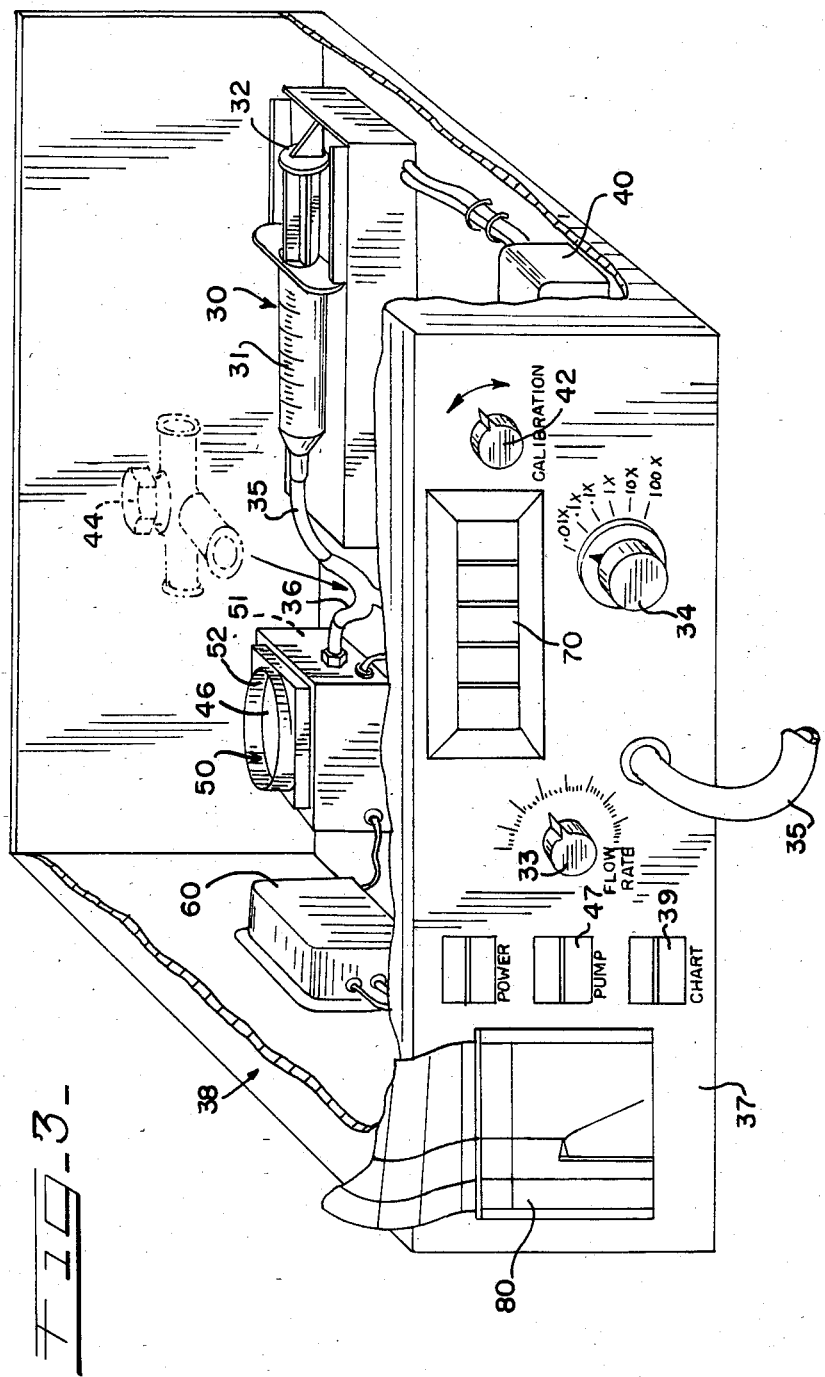

PORTABLE INSTRUMENT TO TEST PRESSURE/FLOW OF VENTRICULAR SHUNT VALVES

BACKGROUND AND SUMMARY OF THE INVENTION

The present invention relates to portable instruments for the testing of valve characteristics and, more particularly, to a portable testing system for the purpose of testing implantable valves to determine the pressure and flow characteristics of these valves. In particular, this invention is useful in the testing of ventricular shunt valves immediately prior to surgical implantation.

The variety and number of implantable valves used to treat medical conditions in the human body has increased tremendously over the past decade. Hydrocephalus is one such medical condition that often requires the use of a valve implanted into the patient's body, particularly within the brain tissue. Hydrocephalus is the general term that characterizes the condition in which the body, for any one of a variety of reasons, is unable to relieve itself of excess cerebrospinal fluid (CSF) collected in open spaces (ventricles) that are found in the brain. Excessive collection of the CSF in the brain ventricular spaces can and quite often does result in an increase in pressures on the brain both radially outwardly and radially inwardly. Acute or unexpected increases in these brain pressures are known to cause a number of adverse physiological effects including compression of brain tissue, internal blood flow in the brain tissue, and impairment of the normal metabolism of the brain.

Treatment of a hydrocephalic condition therefore requires the relief of any abnormally high pressures that may arise within the skull. This is most easily accomplished by providing a means for the drainage of the excess fluid. As a result, a variety of valves for the use in CSF pressure regulator systems and in methods of controlling CSF pressure have been developed. These valves can take various forms such as single and dual check valves, servo valves or combinations thereof. Since CSF is essentially an ultrafiltrate of blood, such valves usually divert CSF from the ventricles of the brain through a discharge line to a suitable drainage area within the patient's body, such as the venous system or the peritoneal cavity. However, the CSF can also be directed to an area exterior of the body so that the flow of the fluid can be monitored and the fluid contents analyzed. Check valves are most often used in these drainage systems and these valves operate by opening when the difference between the pressure of the CSF within the cranial area of the patient exceeds the pressure in the outlet or discharge line.

Valves that are implantable in the body therefore require testing to determine their operating characteristics such as the pressures at which the valve will open and close for given flow rates. These characteristics can then be compared to the patient's requirements and may also be helpful in providing a confirmation of the valve design specifications prior to implantaion. The operating characteristics of an implantable valve encompass both the pressures at which the valve will open continuously, and the pressures at which the valve will only open momentarily for intermittent flow and discharge the excess CSF fluid. With these characteristics before him, the surgeon can then make any necessary adjustments in the valve, if the valve is of the adjustable type, to match the requirements of the patient prior to implantation while in the operating room.

It therefore becomes desirable to provide a system for the testing of implantable valves. It further becomes desirable to provide a portable and compact system for testing implantable valves for use within the operating room. Additionally, it is also desirable to provide a portable testing system for implantable valves in which the testing medium is a gaseous fluid rather than a liquid fluid which is the typical testing medium for such valve testing systems. Utilizing a liquid testing medium requires providing a reservoir of the liquid testing medium and maintaining the sterility of such a liquid testing fluid.

The present invention is directed to a system for the testing of implantable valves using air or a similar gaseous fluid as a testing medium to determine the pressure and flow characteristics of such valves. In such a testing system, a pump is provided to pump a testing fluid drawn from the testing environment under sterile conditions, through the implantable valve. A control mechanism is attached to the pump for providing a variety of constant flow rates so that the characteristics of the valve can be determined under a variety of operating conditions. A pressure transducer that utilizes atmospheric pressure as a reference senses the changes in the air pressure in the valve. The transducer is coupled to a signal generator which generates a signal that is received by a recording instrument. The recording instrument preferably is provided with both a digital display recorder and a chart recorder or plotter to provide a permanent record of the pressure/flow characteristics of the valve which may be preserved and attached to the patient's chart.

The use of air or similar gaseous fluid as a testing medium dispenses with the need for a liquid fluid reservoir thus giving the testing system of the present invention its desired portability. By the use of air or the like for testing purposes, the need to dry or disinfect the valve is eliminated. A filter element that includes a bacteriostatic filter may be provided between the valve and the pump to prevent entrance of any airborne contaminants into the valve. Typically, sterile tubing will be used in the system so that the pressures and pressure versus flow characteristics can be determined in a sterile field such as that which one obtains in an operating room.

In view of the foregoing, it is a general object of the present invention to provide a new and improved system for testing the pressure/flow characteristics of implantable valves.

It is another object of the present invention to provide a portable test system for the testing of the pressure/flow characteristics of ventricular shunt valves utilizing a gaseous fluid as a testing medium.

It is a further object of the present invention to provide a portable instrument system for testing the pressure/flow characteristics of ventricular shunt valves in which the test system includes a single pressure sensing device having atmospheric pressure as a reference point.

It is yet a further object of the present invention to provide a portable instrument system for testing the pressure/flow characterisitcs of implantable ventricular shunt valves having a variety of selectable constant flow rates for delivering air to a surgically implantable valve such that the valve can be calibrated within the sterile field of an operating room.

It is still a further object of the present invention to provide a portable testing system for the testing of implantable valves wherein the testing system may be placed outside the sterile field of the operating room and by sterile fluid communication means, an implantable valve can be tested in the operating room without breaking the sterile field.

BRIEF DESCRIPTION OF THE DRAWINGS

The features of the present invention which are believed to be novel are set forth with particularity in the appended claims. The invention, together with further objects and advantages thereof, may best be understood by reference to the following description taken in conjunction with the accompanying drawings, in which reference numerals identify like elements, and in which:

FIG. 3 is a cut-away perspective view of the embodiment of FIG. 2; and

DESCRIPTION OF THE PREFERRED EMBODIMENT

Figure 1:
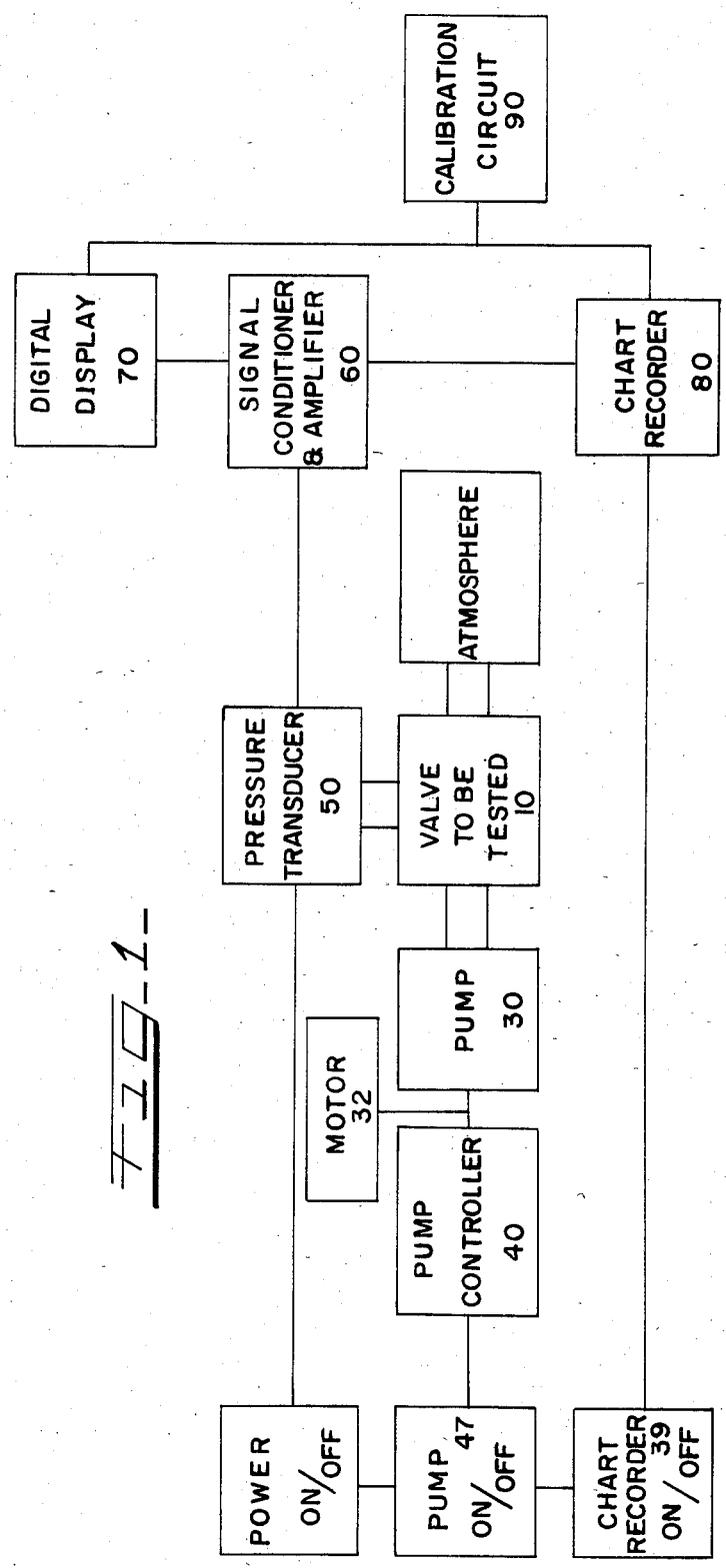
FIG. 1 is a schematic view showing a general arrangement of components of a portable testing system constructed in accordance with the invention and useful in understanding the operation thereof.

Due to the required small size and relatively low working pressure and volumes encountered in hydrocephalic conditions, implantable valves that are used in the treatment thereof commonly incorporate a simple check valve in which a valve element or orifice plate works against a valve seat to control flow through the valve. A check valve is a valve which will stop the flow of fluid in one direction but will allow flow in the opposite direction. In a condition of hydrocephalus, an implantable valve permits fluid in the ventricular spaces of the brain to flow outwardly through a discharge catheter or conduit to a body cavity for drainage. As such, check valves are significantly responsive to the pressure differential across the valve. In this regard, they are responsive to both the valve inlet pressure and the valve outlet pressure. Accordingly, it is particularly desirable to know prior to implantation of the valve, the pressure at which the ventricular shunt valve will initially open and completely open for a specific flow rate.

By applying a pump that is capable of supplying selectively chosen constant flow rates of fluid to the valve, the build-up of pressure behind the valve over time can be accurately monitored so that the cracking pressure, which is the lowest pressure at which a pressure-actuated valve will begin to pass CSF, can be determined for that flow rate. This cracking pressure indicates the threshold limit that the intercranial fluid pressure will achieve before operation of the valve is initiated.

Check valves that are designed for use as ventricular shunt valves typically contain a means for biasing the valve element into a closed position. A valve spring is most commonly used to bias the valve element, which may be a valve plate, disc or ball, and the valve spring is chosen having a force, or spring constant such that at the cracking pressure the spring constant is overcome and the valve will begin to pass CSF through it. If the flow rate increases slightly, the valve spring retracts and allows the valve to open fully allowing full flow through the valve. Consequently, the intercranial pressure drops. If the flow rate remains at a constant or increases, the valve remains in the open position.

When the valve element lifts off of its seat, the system pressure on the valve element (the pressure on the inlet side of the valve corresponding to the intercranial pressure of the patient) reduces to a point at which the spring will again close the valve by forcing the valve element against the seat, shutting off the flow. In this manner, the implantable shunt valve functions as a safety relief valve for sudden momentary accumulations of high CSF pressure within the cranium. Accordingly, the shunt valve size and flow capacity must be adequate to relieve sufficient fluid from the brain ventricles to reduce the maximum system pressure to an acceptable level and consequently close. It is desired that a ventricular shunt valve close promptly and reliably when the CSF pressure regains the acceptable level to prevent drainage of the normal CSF level within the brain, a condition that can lead to the collapse of the ventricles.

It therefore becomes desirable that the surgeon be aware of the operating pressure characteristics for an implantable valve prior to implantation to achieve the best possible results in attending to the special requirements of the individual patient. With the present invention, the surgeon can determine the pressure across the valve element at which an implantable valve will operate for a variety of selected constant flow rates and judge the suitability of the valve for steady increases of CSF as well as any sudden, unexpected build-up of CSF within the ventricles. When used with adjustable implantable valves, the surgeon can set the valve for a desired opening pressure for a constant flow rate. By utilizing air as a testing medium, the system can be made portable for use within the operating room and no delay is encountered in waiting for disinfecting the valve.

Figure 2:
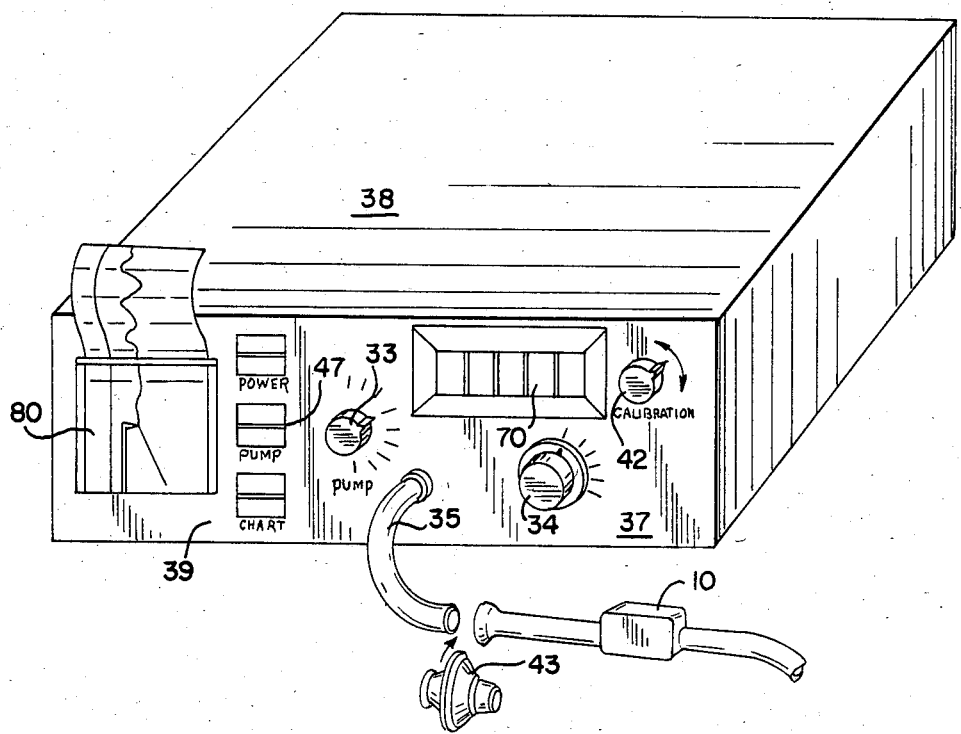
FIG. 2 is a perspective view of the preferred embodiment of the portable testing system.

According to the invention, as described schematically in FIG. 1 and shown in FIGS. 2 and 3, there is provided a portable instrument system for the testing of opening and closing pressures of implantable ventricular shunt valves. The testing system depicted in the Figures includes a rate pump 30 that is capable of supplying a flow of air or other similar gaseous fluid to an implantable valve 10. Rate pump 30 is of the type typically found in the art, and is shown in FIG. 3 as a syringe pump which includes a syringe 31 driven by an electric motor 32. The pump 30 includes means in the form of a pump speed controller 40 for providing various predetermined precise and continuous flow rates such that the flow rate chosen by the operator can remain at a constant value.

A positive displacement pump or a suction pump may be chosen for use in the system to either pump or draw air through the valve. The valve outlet is connected to tubing 35 leading to the pump suction end if air is to be drawn through the valve 10 while the valve inlet is connected to the positive displacement end of the pump if air is to be pumped through the valve 10. In the Figures the rate pump 30 may be capable of acting as either a positive displacement or suction pump, dependent on the direction the motor drives the impeller portion of the syringe.

Three flow rates that have been utilized for the treatment of hydrocephalus are found to be particularly useful in testing implantable valves, these being 1.5, 5.0 and 50.0 milliliters or cubic centimeters per hour (ml/hr. or cc/hr.). Additional flow rates between these values can be chosen by the operator by means of a pump speed adjustment switch 33. Also, a range multiplication circuit, not shown, controlled by a dial 34 may be provided so that other units can be chosen for testing such as microliters per minute.

For testing purposes, the implantable valve 10 is connected to tubing 35 that leads to one end of a 'wye' or 'tee' section 36, which is then connected to the pump 30 by suitable means. The connection 36 may include a three-way stopcock 44 (shown in phantom) capable of providing equal flow rates both to the valve 10 and to a pressure sensing device 50. The stopcock 44 is also capable of operating as a means to isolate the pump 30 from the pressure sensing device 50 for calibration purposes.

With more particular reference to the pressure sensing device 50, such provides means for measuring the air pressure differential across the ventricular shunt valve 10. Typically, the pressure sensing device is a pressure sensor or pressure transducer that is connected to the remaining end of the tubing connection 36 or stopcock 44. The transducer receives the same flow and the same pressure as does the valve 10 and converts the testing fluid pressure to electrical signal as the fluid flows through the tubing and builds up on the face of the valve element. The transducer 50 can incorporate principles well known in the art such as a pressure chamber 51 having a pressure sensing diaphragm 52 sensitive to low and medium pressures therein.

Devices that utilize a liquid fluid as a testing medium require a differential pressure sensing device that needs two transducers located on opposite sides of the valve element, each transducer sensing the pressure of the fluid on each side of the valve element. In an important aspect of the invention, only one transducer is used, a gauge transducer, such transducer being exposed both to the atmosphere and the gaseous testing fluid present in the tubing connection 36.

In FIG. 3, one side of the transducer diaphragm 52 receives the fluid flow from the pump 30 through one end of fluid connection 36 while the opposite side 46 of the diaphragm 52 is exposed to the atmosphere and therefore senses the atmospheric pressure or gauge pressure. This atmospheric pressure is the same pressure that the outlet side of the valve, which is open to the atmosphere (FIG. 4), also receives. By using such a gauge transducer in combination with a gaseous testing fluid, an advantage is obtained over devices that utilize a liquid fluid testing medium in that the use of two differential pressure transducers and the need to dry out and disinfect the valve are eliminated. Additionally, the need for a reservoir of liquid testing fluid is also eliminated, enabling the present invention to be utilized within the operating room environment. Since there is no need to dry or disinfect the valve, the implanting surgeon can test the valve immediately prior to the operation.

In response to the air or testing fluid pressure, the transducer generates an electrical signal which is transmitted to a signal conditioner 60. The signal conditioner 60 amplifies and splits the transducer electrical signal. The split signal is sent by the conditioner 60 to a readout instrument having a digital display 70, conveniently located on the front panel 37 of the system enclosure 38, or after having passed through an analog output (not shown) of the signal conditioner 60, to a graphic chart recorder 80, or both. The chart recorder 80 provides a permanent printed record of the implantable valve 10 characteristics as they are computed and displayed by the readout instrument digital display 70. Both the readout instrument and the chart recorder are well known in the art. An on-off swith 39 may be provided for disabling the chart readout instrument when not required. It will be appreciated that the particular number, grouping and form of the various controls and displays associated with the front panel 37 are provided and arranged as needed, depending upon the placement of the individual components within the enclosure 38.

A calibration circuit 90 that interconnects the digital display 70, chart recorder 80 and signal conditioner 60 is provided to enable the user to establish a reference reading by means of a zero adjustment control 42 to compensate for various temperature variations that may be encountered in the operating range of the device. Calibration or "zeroing" of the transducer can be accomplished by disconnecting the valve 10 from the pump tubing 35. The pump 30 is then shut off by way of control swith 47 and the calibration control dial 42 is adjusted until a zero reading is obtained. At this point any drift in the transducer 50, due to temperature or other variable, has been compensated for. The valve 10 is then connected and the pump 30 turned on.

Figure 4:
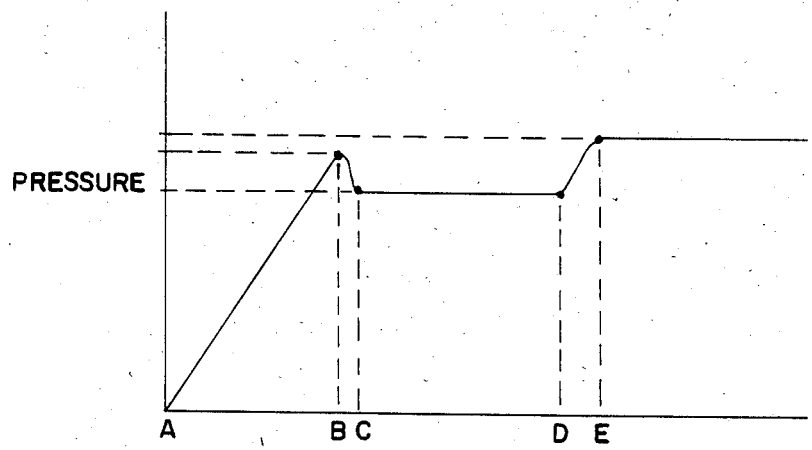
FIG. 4 is a representative chart displaying the pressure in the valve for two different flow rates through the valve against time, which chart is of the type obtained by the preferred embodiment.

A typical pressure-flow chart obtained from the chart recorder 80 for use by the implanting surgeon is illustrated in FIG. 4. The chart indicates the rise in pressure across the valve element over time for two flow rates. The section of the graph found between points A and B indicate the accumulation of pressure behind the valve element of the implantable valve 10. The peak at point B indicates the "cracking" pressure of the valve 10 at which the valve element just begins to open. As the valve element opens completely, a slight pressure drop becomes evident between points B and C on the chart. The pressure of the fluid through the valve 10 will then remain a constant for a selected flow rate (C–D on the chart). Should the operator select a higher constant flow rate, the pressure in the valve will increase (D–E) until a steady pressure is obtained as at point E, which represents the pressure of the fluid passing across the valve element for the increased flow rate. The pressures on the chart which have units equivalent to inches of water (in. $H_2O$) enable the surgeon to match the operating characteristics of the valve to the special requirements of the patient. The testing process can be repeated for the same valve to measure the reliability of the valve element to reproduce the opening pressure. Additionally, any intermittent peaks on the chart may indicate irregularities in the valve manufacture.

By reason of its elimination of a liquid fluid reservoir, the testing system of the present invention is portable. The components of the system can be arranged in any arbitrary manner within the system enclosure 38 such that the system can be inserted into a carrying case for ease of transportation. The dimensions for such a system are typically $9 \times 5 \times 24$ inches with the system having a weight of approximately 20 lbs. The system's portability enables it to be used either within the sterile environment of the operating room or positioned immediately outside the sterile field. In the latter situation, additional lengths of sterile tubing may be provided to connect the rate pump 30 to the valve 10. Additionally, a filter element 43 containing a bacteriostatic or micropore filter is positioned between the valve 10 and the pump 30, when a positive displacement pump is used (FIG. 3), or between the valve 10 and the atmosphere when a suction pump is used in order to prevent the possibility of delayed infection due to the introduction of any airborne contaminants into the valve 10.

The need for sterilizing or disinfecting the implantable valve by a high temperature liquid bath is also eliminated. By use of the present invention, the implanting surgeon can readily verify that the operating pressure of the ventricular shunt valve is equal to the desired CSF pressure. If the valve 10 does not meet the patient's medical needs, the valve 10 can either be adjusted until the desired operating pressure for a specific flow rate is achieved or another valve may be selected for implantation.

The foregoing description of the invention is intended to illustrate the principles and features thereof and should not be understood to limit the invention, since modifications and variations would suggest themselves to those skilled in the art without departing from the spirit of the invention, the scope of which is set forth in the appended claims.

What is claimed is:

1. A portable instrument for testing the pressure and flow characteristics of an implantable valve with a gaseous testing fluid in a substantially liquid-free testing atmosphere, said valve having an inlet port, an outlet port and a fluid passageway connecting said inlet port and said outlet port, the fluid passageway having a valve element for controlling the flow of fluid through the fluid passageway, the system comprising, in combination:
   means for pumping a gaseous testing fluid through the valve at a predetermined flow rate;
   means for maintaining the flow rate of the testing fluid at a constant rate while pumping said testing fluid through said implantable valve;
   means for directing the testing fluid both to said implantable valve and to a single pressure sensing device, said pressure sensing device receiving the testing fluid at the same predetermined flow rate as that received by said valve;
   said pressure sensing device including a single pressure transducer having a diaphragm therein, one side of said diaphragm being mechanically coupled to said fluid directing means and the opposite side of said diaphragm being exposed to the testing atmosphere, whereby said transducer measures the difference in pressure between said testing atmosphere and the gaseous testing fluid directed to said valve and said diaphragm, said pressure sensing device further including means for producing an electrical output signal indicative of the testing fluid pressure within said valve passageway; and
   means for conditioning the electrical signal for reception by means for indicating the testing fluid pressure level in said valve passageway.

2. The portable testing instrument of claim 1, wherein said testing fluid directing means includes a fluid connector having an inlet port and two outlet ports and a fluid passageway interconnecting said inlet port with said outlet ports, one of said fluid connector outlet ports being adapted to be in fluid passing communication with said implantable valve, the other of said fluid connector outlet ports being adapted to be in fluid passing communication with said pressure sensing device and said fluid connector inlet port being adapted to be in fluid passing communication with said pumping means.

3. The portable testing instrument of claim 2, wherein said fluid directing means includes a three-way stopcock capable of isolating one of said fluid connector outlet ports from the other one of said fluid connector outlet ports.

4. The portable testing instrument of claim 1, further including means for providing a barrier for preserving the sterility of said valve, said barrier means being located between said valve inlet port and the testing environment.

5. The portable testing instrument of claim 4, wherein said sterility preserving means includes a bacteriostatic filter.

6. The portable testing instrument of claim 1, wherein said fluid communication means includes sterile tubing communicating said pump with said valve.

7. The portable testing instrument of claim 1, further including calibration means capable of adjusting said pressure sensing device to compensate for signal drift, whereby said pressure sensing device can be adjusted to a reference pressure reading.

8. The portable testing instrument of claim 1, further including an amplifier for amplifying said electrical impulse generated by said pressure sensing means.

9. The portable testing instrument of claim 1, wherein one end of said pumping means is open to the environment whereby the atmosphere of the environment is utilized as said gaseous testing fluid.

10. The portable testing instrument of claim 9, wherein said pumping means includes a positive displacement pump, said inlet of said valve being connected to the displacement end of said pump and the outlet of said valve being open to the environment, said testing fluid being pumped through said valve by said positive displacement pump.

11. The portable testing instrument of claim 9, said pumping means includes a suction pump and the outlet of said valve is connected to the suction end of said pump and said inlet of said valve is open to the environment, whereby said pump draws the testing fluid from the environment through said valve.

12. A method for the testing of the pressure and flow characteristics of a surgically implantable valve with a gaseous testing fluid in a substantially liquid-free testing atmosphere, said implantable valve being of the type that has a valve inlet port, a valve outlet port and a fluid passageway connecting said inlet and outlet ports, the fluid passageway having a valve element for controlling the flow of fluid through the fluid passageway, comprising the steps of:
   pumping a gaseous testing fluid across the valve element at a predetermined flow rate;
   maintaining the flow rate of the testing fluid at a constant rate while pumping said testing fluid through said implantable valve;
   providing a single pressure sensing device including a gauge pressure transducer having a diaphragm therein, one side of said diaphragm being exposed to said valve testing atmosphere;
   directing the testing fluid both to the implantable valve being tested and to the opposite side of said pressure transducer at the same predetermined flow rate;
   producing an electrical output signal indicative of the pressure of the testing fluid across said valve element;

conditioning the electrical signal for reception by a means for indicating the level of pressure of the testing fluid across the valve element, and indicating the pressure of the testing fluid across the valve element.

13. The method of claim 12, wherein said fluid directing step includes providing a fluid connector having an inlet port and two outlet ports and a fluid passageway therebetween interconnecting said inlet port with said outlet ports, communicating one of said fluid connector outlet ports with said implantable valve, communicating the other of said fluid connector outlet ports with said pressure sensing device, and communicating the inlet port of said fluid connector with a pump.

14. The method of claim 13, further including selectively isolating one of said fluid connector outlet ports from the other one of said fluid connector outlet ports.

15. The method of claim 12, further including the step of providing a barrier preserving the sterility of said valve during said testing by locating a sterile barrier between the inlet port of said valve and the testing environment.

16. The method of claim 12, wherein said fluid directing step measures the difference between the pressure across said valve element and the pressure of a testing environment.

17. The method of claim 12, further including the step of adjusting the pressure sensing device to a pressure reading equal to the pressure of the testing environment for a reference.

18. The method of claim 12, wherein said fluid directing step includes drawing said gaseous testing fluid from the testing environment.

* * * * *

UNITED STATES PATENT AND TRADEMARK OFFICE
CERTIFICATE OF CORRECTION

PATENT NO. : 4,598,579
DATED : July 8, 1986
INVENTOR(S) : Joel Cummings and Michael D. Hooven It is certified that error appears in the above—identified patent and that said Letters Patent is hereby corrected as shown below:

On cover page, under U.S. Patent Documents, fourth item, "El-Shafel" should read --El-Shafei--; fifth item, "4,156,442" should read --4,156,422--.
On cover page, under Other Publications, fourth item, "19895" should read --1985--.
Column 1, line 61, "implantaion" should read --implantation--.
Column 6, line 23, "swith" should read --switch--.
Column 8, line 5, "ports." should read --port.--; line 57, delete "sensing".

Signed and Sealed this
Fourteenth Day of October, 1986

[SEAL]

*Attest:*

DONALD J. QUIGG

*Attesting Officer*   *Commissioner of Patents and Trademarks*